(12) United States Patent
Poore (10) Patent No.: US 8,571,683 B2
(45) Date of Patent: Oct. 29, 2013

(54) MRI RF REJECTION MODULE FOR IMPLANTABLE LEAD

(75) Inventor: John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 759 days.

(21) Appl. No.: 12/557,408

(22) Filed: Sep. 10, 2009

(65) Prior Publication Data

US 2011/0060394 A1    Mar. 10, 2011

(51) Int. Cl.
*A61N 1/08* (2006.01)

(52) U.S. Cl.
USPC ......................................................... 607/116

(58) Field of Classification Search
USPC ......................................................... 607/116
See application file for complete search history.

(56) References Cited

U.S. PATENT DOCUMENTS

| | | | |
|---|---|---|---|
| 3,423,517 A * | 1/1969 | Arrhenius | 174/256 |
| 6,223,419 B1 * | 5/2001 | Abramov | 29/602.1 |
| 6,284,080 B1 * | 9/2001 | Haq et al. | 156/89.16 |
| 6,433,653 B1 | 8/2002 | Matsumura et al. | |
| 6,486,529 B2 | 11/2002 | Chi et al. | |
| 2006/0200218 A1 * | 9/2006 | Wahlstrand | 607/116 |
| 2006/0247684 A1 | 11/2006 | Halperin et al. | |
| 2007/0112398 A1 | 5/2007 | Stevenson et al. | |
| 2007/0288058 A1 | 12/2007 | Halperin et al. | |
| 2008/0269591 A1 | 10/2008 | Halperin et al. | |

FOREIGN PATENT DOCUMENTS

| | | |
|---|---|---|
| WO | 2007145671 A2 | 12/2007 |
| WO | 2007145671 A3 | 12/2007 |

OTHER PUBLICATIONS

Spectrum Semiconductor Materials homepage. <http://www.spectrum-semi.com/index.html> Aug. 2003. Retrieved from www.archive.org Sep. 9, 2012.*

* cited by examiner

*Primary Examiner* — Carl H Layno
*Assistant Examiner* — Luther Behringer (57) ABSTRACT

A high Q self-resonant inductor and method for manufacturing the same is disclosed herein for use in an implantable medical lead. The method of manufacture includes depositing a first conductive material over an elongated ceramic member and removing portions of the conductive material to leave a continuous helical metallic pattern on an elongated ceramic structure. The helical metallic pattern has a first terminal end located at a proximal end of the elongated ceramic member and a second terminal end located at a distal end of the ceramic member. The method also includes covering the helical metallic pattern with a ceramic material to form a first ceramic layer and forming vias in the ceramic material. At least one electrode is coupled to the helical metallic pattern through the vias in the ceramic material.

14 Claims, 9 Drawing Sheets

MRI RF REJECTION MODULE FOR IMPLANTABLE LEAD

FIELD OF THE INVENTION

The present invention relates to implantable medical leads. More specifically, the present invention relates to implantable medical leads having self resonant inductors with high interwind capacitance and low series resistance. The present invention also relates to methods of manufacturing such leads.

BACKGROUND OF THE INVENTION

Existing implantable medical leads for use with implantable pulse generators, such as neurostimulators, pacemakers, defibrillators or implantable cardioverter defibrillators ("ICD"), are prone to heating and induced current when placed in the strong magnetic (static, gradient and RF) fields of a magnetic resonance imaging ("MRI") machine. The heating and induced current are the result of the lead acting like an antenna in the magnetic fields generated during a MRI. Heating and induced current in the lead may result in deterioration of stimulation thresholds or, in the context of a cardiac lead, even increase the risk of cardiac tissue damage and perforation.

Over fifty percent of patients with an implantable pulse generator and implanted lead require, or can benefit from, a MRI in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

There is a need in the art for an implantable medical lead configured for improved MRI safety. There is also a need in the art for methods of manufacturing and using such a lead.

BRIEF SUMMARY OF THE INVENTION

A method of manufacturing an implantable medical lead is disclosed herein. In one embodiment, the method includes: manufacturing a high Q self resonant inductor and providing the self resonant inductor in a lead body. The steps for manufacturing the self resonant inductor includes: a) depositing a first layer of conductive material over an elongated ceramic member, b) removing portions of the first layer to leave a first continuous helical metallic pattern on the elongated ceramic structure, the first helical metallic pattern having a first terminal end located at a proximal end of the ceramic member and a second terminal end located at a distal end of the ceramic member, and c) covering the helical metallic pattern with a ceramic material to form a first ceramic layer. In providing the self resonant inductor in the lead body, the first terminal end is placed in electrical communication with an electrical conductor extending through the lead body from a lead connector end of the lead body, and the second terminal end is placed in electrical communication with an electrode located near a distal end of the lead body.

An implantable medical lead is also disclosed herein. In one embodiment, the lead includes a high Q self-resonant inductor and a lead body. The self resonant inductor may include a first layer comprising: a first helical metallic member located on an elongated member, the first helical metallic member comprising a first terminal end located near a proximal end of the elongated member and a second terminal end located near a distal end of the elongated member; and a dielectric ceramic material coaxially covering the elongated member and the first helical metallic member, the dielectric ceramic material encapsulating the first helical metallic member and having first and second apertures located over the first and second terminal ends, respectively, of the first metallic helical member such that the terminal ends are accessible through the apertures. The lead body may include a lead connector end on a proximal end of the lead body and an electrode on a distal end of the lead body. The lead connector end may include an electrical contact. The self resonant inductor may be supported on the lead body. The first terminal may be in electrical communication with the electrical contact of the lead connector end via a first electrical pathway extending through the first aperture. The second terminal may be in electrical communication with the electrode via a second electrical pathway extending through the second aperture.

Another implantable medical lead is also disclosed herein. In one embodiment, the lead includes a body and an electrical pathway. The body may include a distal portion with an electrode and a proximal portion with a lead connector end. The electrical pathway may extend between the electrode and lead connector end. The electrical pathway may include a self resonant inductor, wherein the self resonant inductor comprises one or more layers comprising a helical metallic pattern on a dielectric ceramic material and a ceramic layer coaxially covering the helical metallic pattern.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is an implantable medical lead employing a parallel capacitor inductor circuit (also called a tank circuit or a self resonant inductor) wherein the tank circuit is implemented as a high Q inductor that utilizes a high dielectric constant ceramic insulation between winds of the inductor that results in reduced size, manufacturing repeatability and Q adequate to adequately block MRI RF energy. The high Q self resonant inductor may be utilized in implantable medical leads that may be exposed to certain frequencies during an MRI scan. The Hi-K insulation increases capacitance between the winds of the self resonant inductor and, hence, fewer turns are required to achieve resonance at MRI frequencies, e.g., 64 MHz for current 1.5 Tesla MRI systems and 128 MHz for current 3.0 Tesla MRI systems. Specifically, the relationship between inductance, resistance and capacitance at a resonant frequency may be represented by the equation $L(resonance)=1/((2\pi f(resonance))^2 C)$; where L is the inductance at resonance, f is the resonant frequency, and C is the capacitance. As those of skill will recognize, L and C are inversely related and, thus, as C increases L decreases. With the Hi-K insulation between winds, C is relatively higher than in conventional inductors resulting in a lower L and fewer turns in the self resonant inductor resulting in lower effective resistance. The decrease in resistance results in reduced $I^2R$ heating during MRI RF application.

Figure 1:
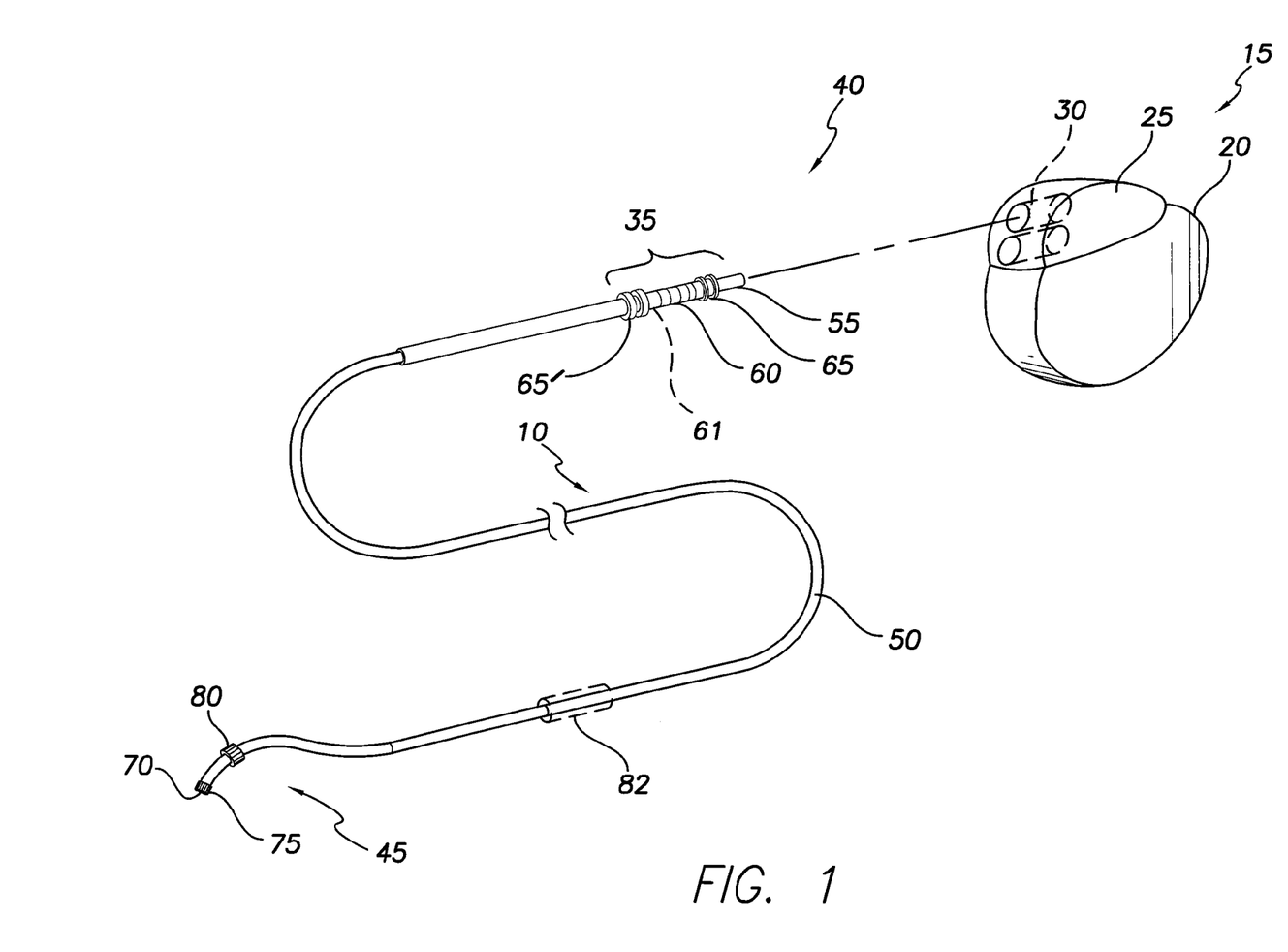
FIG. 1 is an isometric view of an implantable medical lead and a pulse generator for connection thereto.

For a general discussion of an embodiment of a lead 10 employing the tank circuit or self resonant inductor 160, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30. Although only a single lead is illustrated, it can be appreciated that multiple leads may be implemented. In particular, for example, for CRT treatments, there may be leads for both the right and left ventricle.

As shown in FIG. 1, in one embodiment, the lead 10 may include a proximal end 40, a distal end 45 and a tubular body 50 extending between the proximal and distal ends. The lead 10 may be configured for a variety of uses. For example, the lead 10 may be a RA lead, RV lead, LV Brady lead, RV Tachy lead, intrapericardial lead, etc.

As indicated in FIG. 1, the proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75 and a ring electrode 80. In some embodiments, the lead body 50 is configured to facilitate passive fixation and/or the lead distal end 45 includes features that facilitate passive fixation. In such embodiments, the tip electrode 75 may be in the form of a ring or domed cap and may form the distal tip 70 of the lead body 50.

Figure 2:
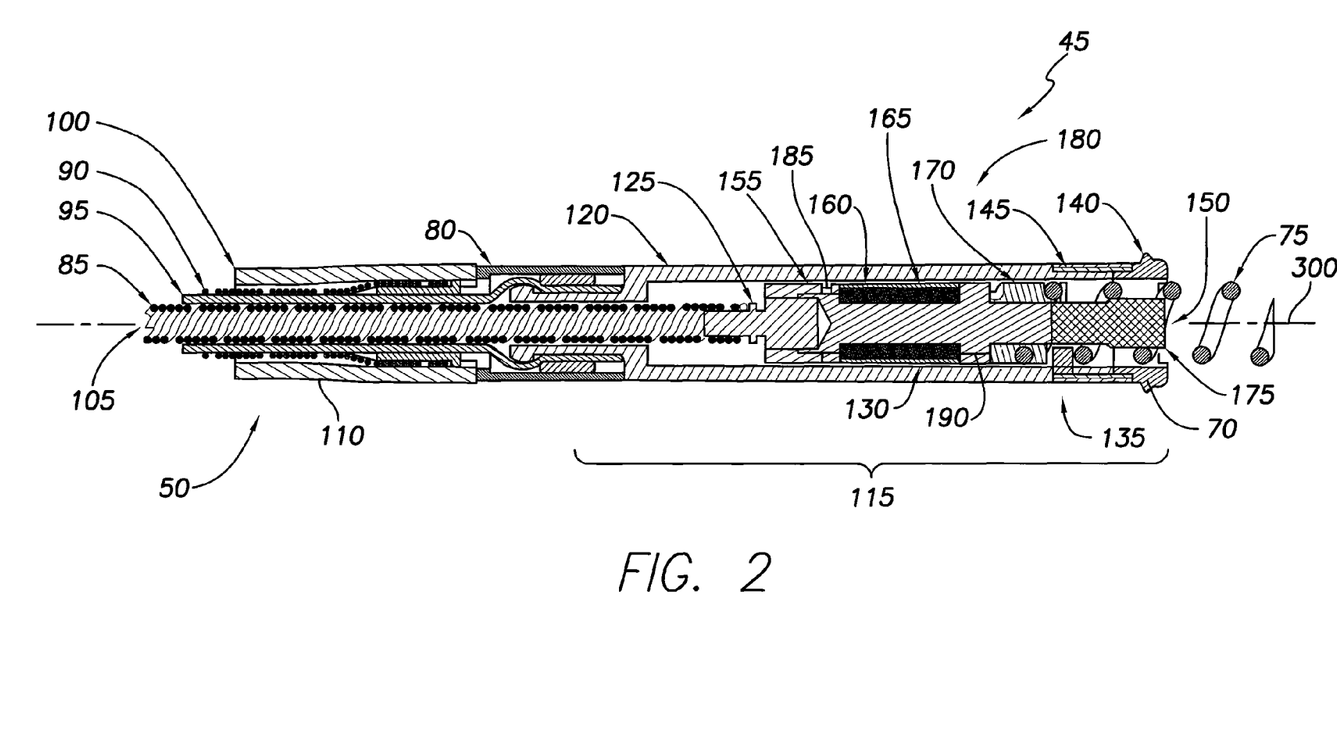
FIG. 2 is a longitudinal cross-section of a lead distal end.

As shown in FIG. 2, which is a longitudinal cross-section of the lead distal end 45, in some embodiments, the tip electrode 75 may be in the form of a helical anchor 75 that is extendable from within the distal tip 70 for active fixation and serving as a tip electrode 75.

As shown in FIG. 1, in some embodiments, the distal end 45 may include a defibrillation coil 82 about the outer circumference of the lead body 50. The defibrillation coil 82 may be located proximal of the ring electrode 70.

The ring electrode 80 may extend about the outer circumference of the lead body 50, proximal of the distal tip 70. In other embodiments, the distal end 45 may include a greater or lesser number of electrodes 75, 80 in different or similar configurations.

As can be understood from FIGS. 1 and 2, in one embodiment, the tip electrode 75 may be in electrical communication with the pin contact 55 via a first electrical conductor 85, and the ring electrode 80 may be in electrical communication with the first ring contact 60 via a second electrical conductor 90. In some embodiments, the defibrillation coil 82 may be in electrical communication with the second ring contact 61 via a third electrical conductor. In yet other embodiments, other lead components (e.g., additional ring electrodes, various types of sensors, etc.) (not shown) mounted on the lead body distal region 45 or other locations on the lead body 50 may be in electrical communication with a third ring contact (not shown) similar to the second ring contact 61 via a fourth electrical conductor (not shown). Depending on the embodiment, any one or more of the conductors 85, 90 may be a multi-strand or multi-filar cable or a single solid wire conductor run singly or grouped, for example in a pair.

As shown in FIG. 2, in one embodiment, the lead body 50 proximal of the ring electrode 80 may have a concentric layer configuration and may be formed at least in part by inner and outer helical coil conductors 85, 90, an inner tubing 95, and an outer tubing 100. The helical coil conductor 85, 90, the inner tubing 95 and the outer tubing 100 form concentric layers of the lead body 50. The inner helical coil conductor 85 forms the inner most layer of the lead body 50 and defines a central lumen 105 for receiving a stylet or guidewire therethrough. The inner helical coil conductor 85 is surrounded by the inner tubing 95 and forms the second most inner layer of the lead body 50. The outer helical coil conductor 90 surrounds the inner tubing 95 and forms the third most inner layer of the lead body 50. The outer tubing 100 surrounds the outer helical coil conductor 90 and forms the outer most layer of the lead body 50.

In one embodiment, the inner tubing 95 may be formed of an electrical insulation material such as, for example, ethylene tetrafluoroethylene ("ETFE"), polytetrafluoroethylene ("PTFE"), silicone rubber, silicone rubber polyurethane copolymer ("SPC"), or etc. The inner tubing 95 may serve to electrically isolate the inner conductor 85 from the outer conductor 90. The outer tubing 100 may be formed of a biocompatible electrical insulation material such as, for example, silicone rubber, silicone rubber-polyurethane-co-polymer ("SPC"), polyurethane, gore, or etc. The outer tubing 100 may serve as the jacket 100 of the lead body 50, defining the outer circumferential surface 110 of the lead body 50.

As illustrated in FIG. 2, in one embodiment, the lead body 50 in the vicinity of the ring electrode 80 transitions from the above-described concentric layer configuration to a header assembly 115. For example, in one embodiment, the outer tubing 100 terminates at a proximal edge of the ring electrode 80, the outer conductor 90 mechanically and electrically couples to a proximal end of the ring electrode 80, the inner tubing 95 is sandwiched between the interior of the ring electrode 80 and an exterior of a proximal end portion of a body 120 of the header assembly 115, and the inner conductor 85 extends distally past the ring electrode 80 to electrically and mechanically couple to components of the header assembly 115 as discussed below.

As depicted in FIG. 2, in one embodiment, the header assembly 115 may include the body 120, a coupler 125, a self resonant inductor assembly 130, and a helix assembly 135. The header body 120 may be a tube forming the outer circumferential surface of the header assembly 115 and enclosing the components of the assembly 115. The header body 120 may have a soft atraumatic distal tip 140 with a radiopaque marker 145 to facilitate the soft atraumatic distal tip 140 being visualized during fluoroscopy. The distal tip 140 may form the extreme distal end 70 of the lead 10 and includes a distal opening 150 through which the helical tip anchor 75 may be extended or retracted. The header body 120 may be formed of polyetheretherketone ("PEEK"), polyurethane, or etc., the soft distal tip 140 may be formed of silicone rubber, SPC, or etc., and the radiopaque marker 145 may be formed of platinum, platinum-iridium alloy, tungsten, tantalum, or etc.

As indicated in FIG. 2, in one embodiment, the self resonant inductor assembly 130 may include a bobbin 155, a self resonant inductor 160 and a shrink tube 165. The bobbin 155 may include a proximal portion that receives the coupler 125, a barrel portion about which the self resonant inductor 160 is located (e.g., wherein the inductor 160 is formed on a hollow tube 215 as described with respect to FIG. 4B later in this Detailed Description), and a distal portion coupled to the helix assembly 135. In an alternative embodiment, the bobbin 155 may be an extension of the self resonant inductor 160 or the self resonant inductor 160 may be formed within the bobbin 155. Such an embodiment may be possible employing the self resonant inductor 160 formed on a solid rod, for example, as described with respect to FIG. 4A later in this Detailed Description. In either case, the bobbin 155 may be formed of an electrical insulation material such as PEEK, polyurethane, or etc.

As illustrated in FIG. 2, the shrink tube 165 may extend about the self resonant inductor 160 to generally enclose the self resonant inductor 160 within the boundaries of the bobbin 155 and the shrink tube 165. The shrink tube 165 may act as a barrier between the self resonant inductor 160 and the inner circumferential surface of the header body 120. Also, the shrink tube 165 may be used to form at least part of a seal about the self resonant inductor 160. The shrink tube 165 may be formed of fluorinated ethylene propylene ("FEP"), polyester, or etc.

As shown in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85, the inner coil conductor 85 and the coupler 125 being mechanically and electrically coupled to each other. The coupler 125 may be formed of MP35N, platinum, platinum iridium alloy, stainless steel, or etc.

As indicated in FIG. 2, the helix assembly 135 may include a base 170, the helical anchor electrode 75, and a steroid plug 175. The base 170 forms the proximal portion of the assembly 135. The helical anchor electrode 75 forms the distal portion of the assembly 135. The steroid plug 175 may be located within the volume defined by the helical coils of the helical anchor electrode 75. The base 170 and the helical anchor electrode 75 are mechanically and electrically coupled together. The distal portion of the bobbin 155 may be received in the helix base 170 such that the bobbin 155 and the helix base 170 are mechanically coupled to each other. The base 170 of the helix assembly 135 may be formed of platinum, platinum-iridium alloy, MP35N, stainless steel, or etc. The helical anchor electrode 75 may be formed of platinum, platinum-iridium ally, MP35N, stainless steel, or etc.

As illustrated in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85 such that the inner coil conductor 85 and the coupler 125 are both mechanically and electrically coupled to each other. The coupler 125 may be formed of MP35N, stainless steel, or etc.

As can be understood from FIG. 2 and the preceding discussion, the coupler 125, self resonant inductor assembly 130, and helix assembly 135 are mechanically coupled together such that these elements 125, 130, 135 of the header assembly 115 do not displace relative to each other. Instead these elements 125, 130, 135 of the header assembly 115 are capable of displacing as a unit relative to, and within, the body 120 when the inner coil 85 is caused to rotate relative to the rest of the lead body by rotation of the pin contact 55 relative to the rest of the lead connector end 35. In other words, these elements 125, 130, 135 of the header assembly 115 form an electrode-self resonant inductor assembly 180, which can be caused to displace relative to, and within, the header assembly body 120 when the inner coil 85 is caused to rotate via rotation of the pin contact 55 electrically and mechanically coupled to the proximal end of the inner coil 85. Specifically, rotation of the electrode-self resonant inductor assembly 180 via rotation of the pin contact 55 in a first direction causes the electrode-self resonant inductor assembly 180 to displace distally, and rotation of the electrode-self resonant inductor assembly 180 via rotation of the pin contact 55 in a second direction causes the electrode-self resonant inductor assembly 180 to retract into the header assembly body 120. Thus, causing the electrode-self resonant inductor assembly 180 to rotate within the body 120 in a first direction causes the helical anchor electrode 75 to emanate from the tip opening 150 for screwing into tissue at the implant site. Conversely, causing the electrode-self resonant inductor assembly 180 to rotate within the body 120 in a second direction causes the helical anchor electrode 75 to retract into the tip opening 150 to unscrew the anchor 75 from the tissue at the implant site.

Figure 4A:
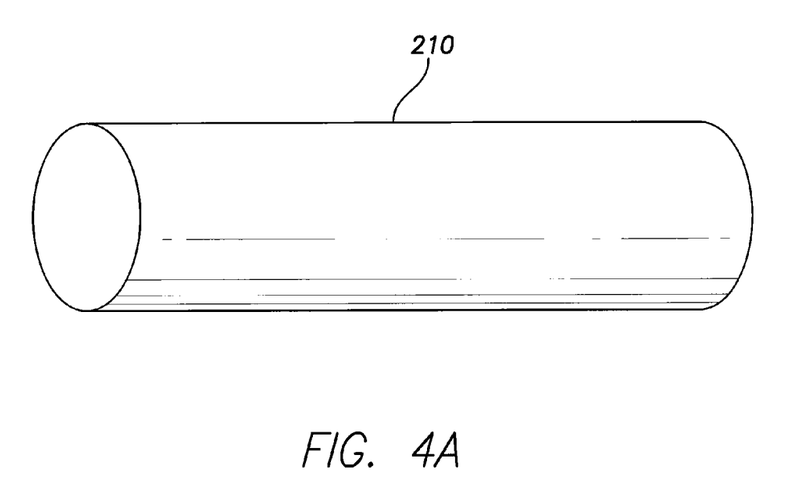
FIGS. 4A and 4B illustrate a ceramic rod and a ceramic tube, respectively, in accordance with alternative embodiments of the present disclosure.
Figure 4B:
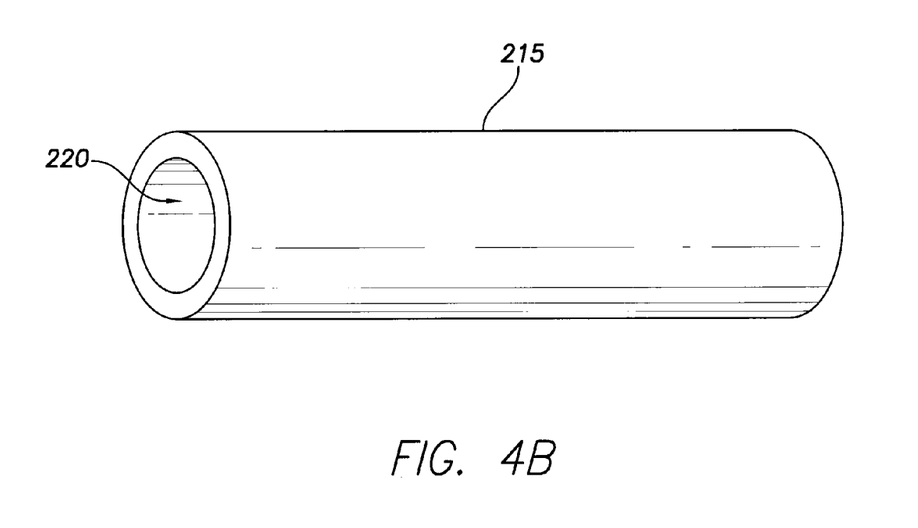

As already mentioned and indicated in FIG. 2, the self resonant inductor 160 may be positioned about the barrel portion of the bobbin 155 when the self resonant inductor 160 is formed about a hollow tube 215, as described later on in this Detailed Description with respect to FIG. 4B, or the self resonant inductor 160 may be formed into the bobbin 155 when the self resonant inductor 160 is formed from a solid rod 210, as described later in this Detailed Description with respect to FIG. 4A. A proximal end 185 of the self resonant inductor 160 may extend through the proximal portion of the bobbin 155 to electrically couple with the coupler 125, and a distal end 190 of the self resonant inductor 160 may extend through the distal portion of the bobbin 155 to electrically couple to the helix base 170. Thus, in one embodiment, the self resonant inductor 160 is in electrical communication with the both the inner coil conductor 85, via the coupler 125, and the helical anchor electrode 75, via the helix base 170. Therefore, the self resonant inductor 160 acts as an electrical pathway through the electrically insulating bobbin 155 between the coupler 125 and the helix base 170. In one embodiment, all electricity destined for the helical anchor electrode 75 from the inner coil conductor 85 passes through the self resonant inductor 160 such that the inner coil conductor 85 and the electrode 75 both benefit from the presence of the self resonant inductor 160, the self resonant inductor 160 acting as a lumped self resonant inductor 160 when the lead 10 is present in a magnetic field of a MRI.

As the helix base 170 may be formed of a mass of metal, the helix base 170 may serve as a relatively large heat sink for the self resonant inductor 160, which is physically connected to the helix base 170. Similarly, as the coupler 125 may be formed of a mass of metal, the coupler 125 may serve as a relatively large heat sink for the self resonant inductor 160, which is physically connected to the coupler 125.

Figure 3:
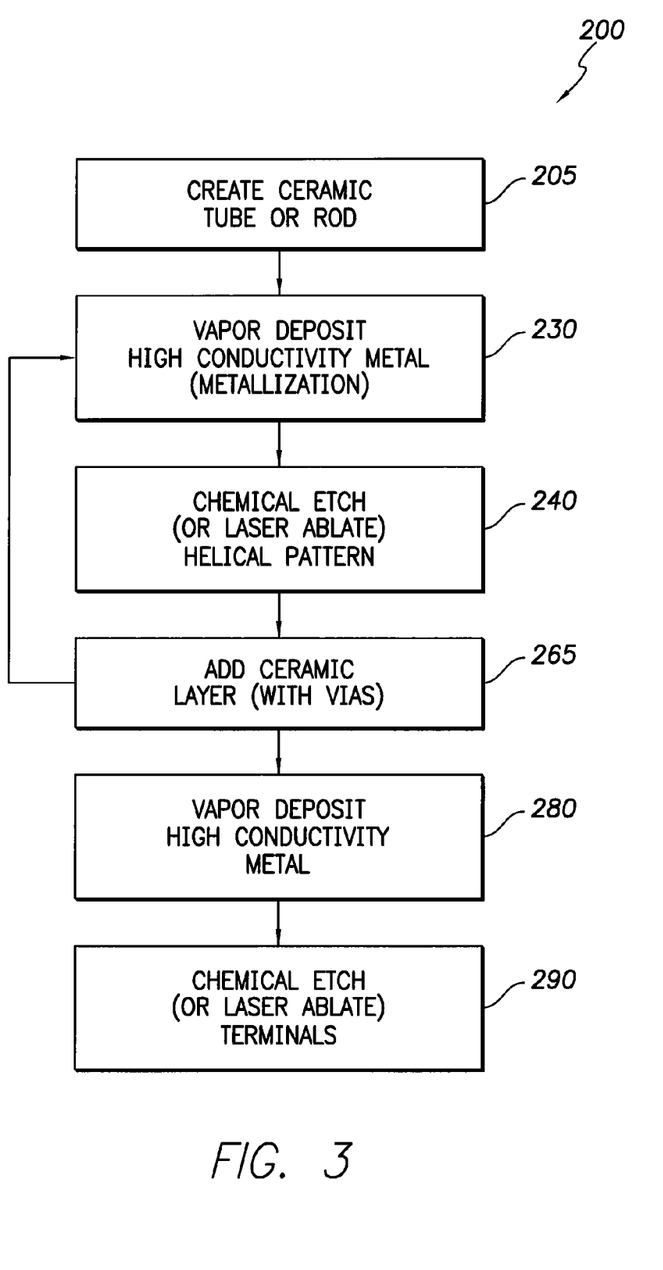
FIG. 3 is a flowchart illustrating an example method for manufacturing a self resonant inductor in accordance with an embodiment of the present disclosure.

As previously mentioned, the self resonant inductor 160 is a high Q self resonant inductor. Generally, a high Q self resonant inductor refers to the quality and efficiency of the self resonant inductor at a given frequency. The higher the Q value of a self resonant inductor, the more ideal the self resonant inductor. Q may be calculated by the following equation $Q=\omega L/R$, where $\omega L$ is reactance at resonance and R is the internal electrical resistance. The resistance R results from the windings of the metal forming the coil and is referred to as series resistance. During operation, the resistance converts electrical current to heat. Reduction of the resistance of the windings results in a higher Q. Additionally, increasing the capacitive and/or inductive reactance of a self resonant inductor increases the Q factor. The following discussion describes a method for manufacturing the high Q self resonant inductor 160 of the lead 10. In particular, FIG. 3 is a flowchart illustrating a technique 200 that includes providing Hi-K insulation between winds of the inductor helix to increase capacitance and, thereby, decrease inductance and resistance for a given resonant frequency. It should be noted, however, that there may be alternative ways to achieve the high Q self resonant inductor other than the method described below and represented in FIG. 3.

Referring to FIG. 3, the technique 200 may begin by creating or providing a ceramic rod 210 or tube 215, as indicated at block 205. FIGS. 4A and 4B illustrate the ceramic rod 210 or tube 215, respectively. The rod 210 may generally be a solid ceramic structure, whereas the tube 210 may have a hollow axial region 220, through which, for example, the barrel of the bobbin 155 may extend, as depicted in FIG. 2. Such a hollow axial region of the tube may be employed for the passage of a stylet therethrough. The ceramics used to create the rod 210 or tube 215 may include any suitable material. In some embodiments, the ceramic may be a suitable biocompatible material such as hydroxyapatite, for example, while in other embodiments the ceramic may include silicon carbide or aluminum oxide, for example. Further, the process for creating the rod 210 or tube 215 may include slip casting, tape casting, injection molding, dry pressing, for example, or any other suitable process. The use of the rod 210 or the tube 215 may be application specific. In one embodiment, for example, the tube 215 may be configured to fit over a barrel portion of the bobbin 155. In another embodiment, the rod 210 may form a central portion of the bobbin 155. For the sake of simplicity, however, the following discussion will focus on the rod 210.

Figure 5:
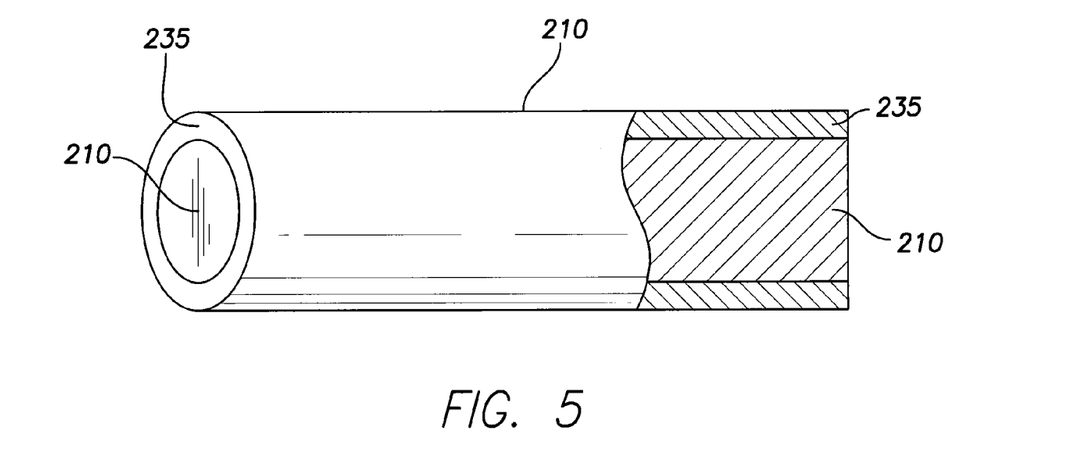
FIG. 5 illustrates the ceramic rod of FIG. 4A having a metallic layer coaxially deposited thereon.

Referring again to FIG. 3, a highly conductive metallic is deposited on the ceramic rod 210, as indicated at block 230. FIG. 5 illustrates the ceramic rod 210 covered with a metallic layer 235. The metallic layer 235 may be applied to the ceramic in any suitable manner, such as vapor deposition, for example, so that the metallic layer 235 and the rod 210 are coaxial. The metallic used to form the metallic layer 235 may be any highly conductive metal including gold, silver, copper, platinum, or any other conductive metal or metallic alloy. In some embodiments, the metallic or metallic alloy used for the metallization is biocompatible. In another embodiment, the metallic is not biocompatible. The use of non-biocompatible metallic is permissible because the metallic layer 235 will be completely covered with ceramic in a later stage of the process.

Figure 6:
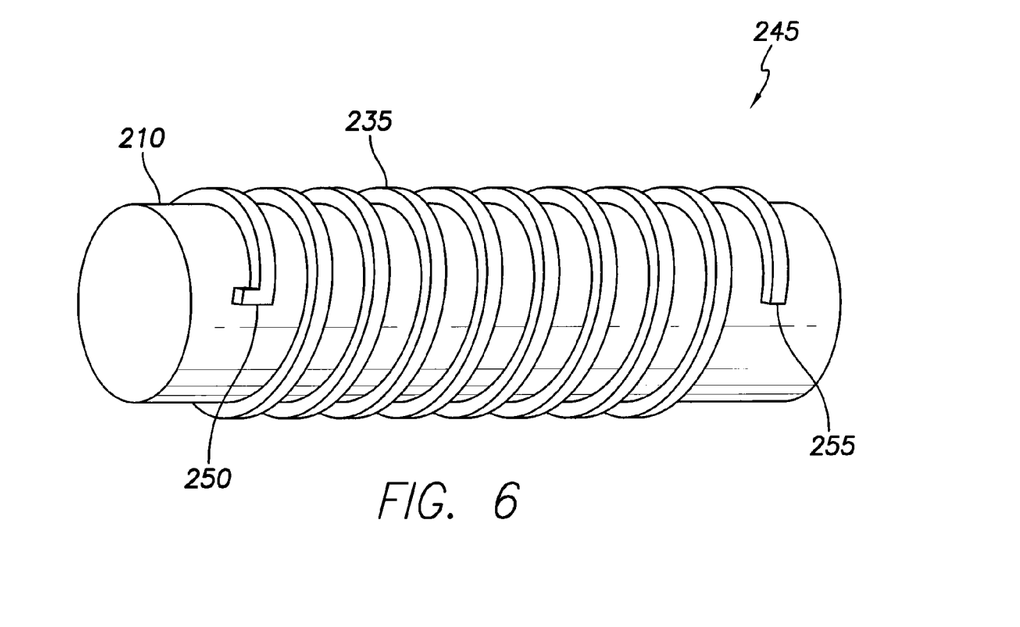
FIG. 6 illustrates the ceramic rod of FIG. 4A after having portions of the metallic layer FIG. 5 removed to leave a helical metallic pattern on the surface of the ceramic rod.

Once the metallic layer 235 has been deposited over the ceramic rod 210, portions of the metallic layer 235 are removed through chemical etch, laser ablation or other suitable process, as indicated at block 240 (FIG. 3). The chemical etching or laser ablation may be performed in accordance with known techniques. The remaining portions of the metallic layer form a helical metallic pattern on the ceramic rod 210, as shown in FIG. 6. It should be understood that the drawings are very generalized diagrammatic representations of possible actual implementations. In particular, the drawings may not present an accurate depiction of size, scale, number of turns, pitch, etc. For example, in an actual implementation, the helical pattern 245 may be tighter, there may be more turns (i.e., revolutions) and the pitch of the helical pattern may be finer.

The left end 250 of the remaining metallization forms a base of a via leading to a terminal or electrical contact 285 of the self resonant inductor 160, the electrical contact 285 being electrically coupled to the distal end of the coupler 125 via an electrical conductor 185 extending from the electrical contact 285 to the distal end of the coupler 125 through the bobbin 155, as shown in FIG. 2. The right end 255 of the helical metallization layer forms a base of a via which extends to another helical metallization layer to be added or, where the metallization layer forming the right end 255 is the outermost metallization layer, the right end 255 forms a base of a via leading to a terminal or electrical contact 285 of the self resonant inductor 160, the electrical contact 285 being electrically coupled to the proximal end of the helix base 170 via an electrical conductor 190 extending from the electrical contact 285 to the proximal end of the helix base 170 through the bobbin 155, as shown in FIG. 2. Whether the right end 255 functions as a via base for a terminal or electrical contact 285 or a via base extending to another metallization layer depends on the number of layers of the self resonant inductor, which may be determined at least in part on the operation parameters of the self resonant inductor.

Figure 7A:
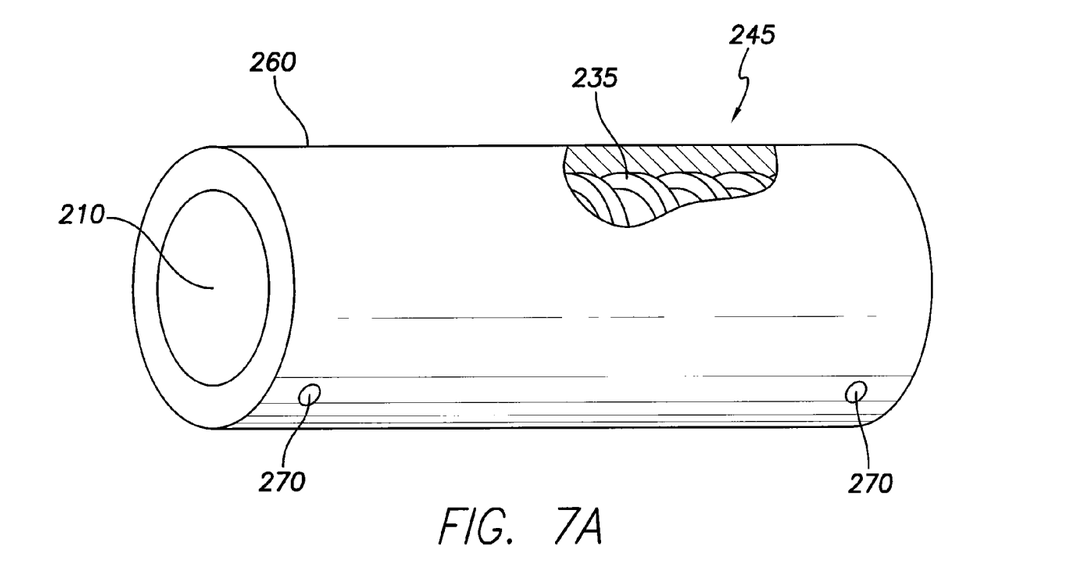
FIGS. 7A and 7B illustrate a ceramic layers covering the helical metallic pattern of FIG. 6 in accordance with alternative embodiments.

A ceramic layer 260 is added over the metallic helix pattern 245, as indicated at block 265 (FIG. 3) and as shown in FIG. 7A. The ceramic layer may be any suitable Hi-K ceramic such as, for example, barium titanite ($Ba_2TiO_3$). A partial cut-out of the ceramic layer 260 is shown in FIG. 7A so that the underlying helical pattern 245 of the metallization layer 235 may be seen. As shown, the ceramic layer 260 completely covers the metallization layer 235 so that the metallization layer 235 is not exposed. The ceramic layer 260 is a high dielectric constant ceramic to increase the interwind capacitance of the underlying inductor helix. The amount of capacitance is inversely proportional to the thickness of the ceramic dielectric layer, directly proportional to the dielectric constant of ceramic material, and directly proportional to the surface area of the electrode on either side of the dielectric.

As will be understood to those of ordinary skill in the art, the high dielectric constant (Hi-K) ceramic increases capacitance between the windings of the self resonant inductor and, hence, fewer turns are required to achieve resonance at MRI frequencies, e.g., 64 MHz for current 1.5 Tesla MRI systems or 128 MHz for current 3.0 Tesla MRI systems. As previously mentioned, the relationship between inductance, resistance and capacitance at a resonant frequency may be represented by the equation $L(resonance)=1/((2\pi f(resonance))^2 C)$; where L is the inductance at resonance, f is the resonant frequency, and C is the capacitance. With the Hi-K insulation provided by the ceramic layer 260 between winds, C is relatively higher than in conventional inductors resulting in a lower L. Thus, fewer turns of the helical metallic pattern 235 may be used in the self resonant inductor resulting in lower effective resistance. The decrease in resistance results in reduced $I^2R$ heating during MRI RF application.

In one embodiment, a single bobbin 155 may be configured for a single frequency. In another embodiment, a single bobbin 155 may be configured to have two wind configurations, wherein one wind is configured for 64 MHz and the other wind is configured for 128 MHz. In yet other embodiments, more than two winds may be present in a single bobbin 155 to address more than two frequencies.

Additionally, as shown in FIG. 7A, vias 270 are provided through the ceramic layer 260 to allow conductive access to the underlying metallic helix 245 and, more specifically, to the via bases 250, 255 of the metallic helix 245 inward from the ceramic layer 260. The vias may be filled by a subsequent metallization process. Specifically, if additional layers of windings are to be provided, steps 230, 240 and 265 may be repeated. As such, the ceramic, metallization, and etching processes may be repeated to create as many ceramic layers, each of said ceramic layers having a respective helical metallization layer 245 imbedded therein and electrically insulated from adjacent helical metallization layers 245, as are needed for a particular application and will depend on the mechanical aspect ratio required of the finished self resonant inductor.

Figure 9:
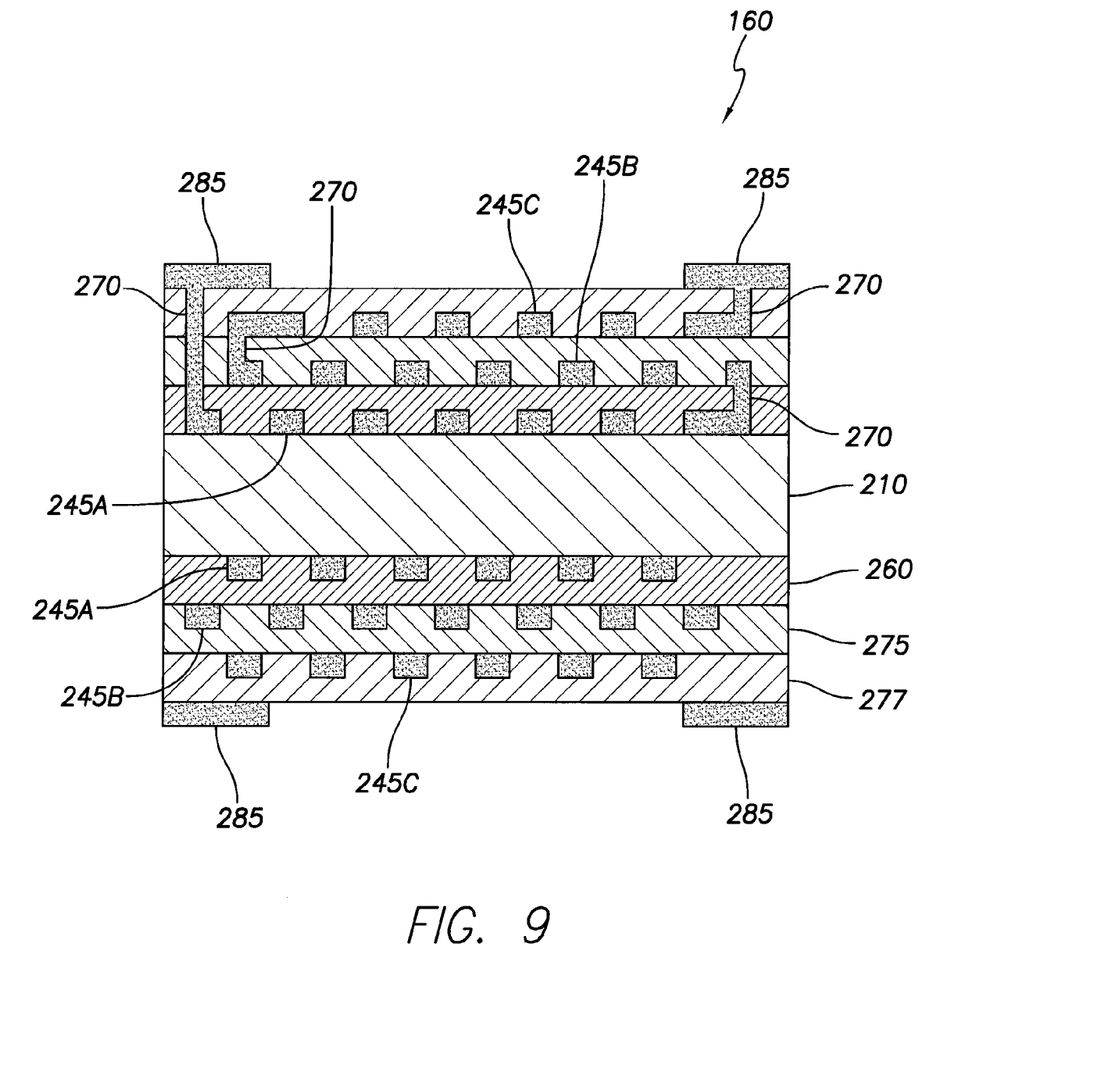
FIG. 9 is a longitudinal cross section of a self resonant inductor having three ceramic layers.

Thus, as can be understood from FIG. 9, which is a longitudinal cross section of an self resonant inductor 160 having three ceramic layers 260, 275, 277, an innermost helical metallization layer 245A extends about the ceramic core 210 and is encased in an innermost ceramic layer 260 also extending about the core 210. Vias 270 at opposite ends of the self resonant inductor 160 extend outward out of the innermost ceramic layer 260, one leading directly through all three ceramic layers 260, 275, 277 to the electrically couple to an electrical contact 285, and the other to electrically couple to the intermediate helical metallization layer 245B extending about the innermost ceramic layer 260. The intermediate helical metallization layer 245B is encased in an intermediate ceramic layer 270 also extending about the innermost ceramic layer 260. Vias 270 near the same end of the self resonant inductor 160 extend outward out of the intermediate ceramic layer 275, one of which is still extending directly through all three ceramic layers 260, 275, 277 to the electrically couple to an electrical contact 285, and the other to electrically couple to the outermost helical metallization layer 245C extending about the intermediate ceramic layer 275. The outermost helical metallization layer 245C is encased in an outermost ceramic layer 277 also extending about the intermediate ceramic layer 275. Vias 270 at opposite ends of the self resonant inductor 160 extend outward out of the innermost ceramic layer 260, one of which is still extending directly through all three ceramic layers 260, 275, 277 to the electrically couple to an electrical contact 285, and the other to electrically couple to the other electrical contact 285 at the other end of the self resonant inductor 160. While the odd-numbered layered self resonant inductor 160 of FIG. 9 has three layers, the process of blocks 230-265 may be repeated as necessary to achieve other odd-numbered configuration (e.g., five ceramic layers, seven ceramic layers, etc.) wherein each via/electrical contact pair ends up on an opposite end of the self resonant inductor 160 from the other via/electrical contact pair.

Figure 7B:
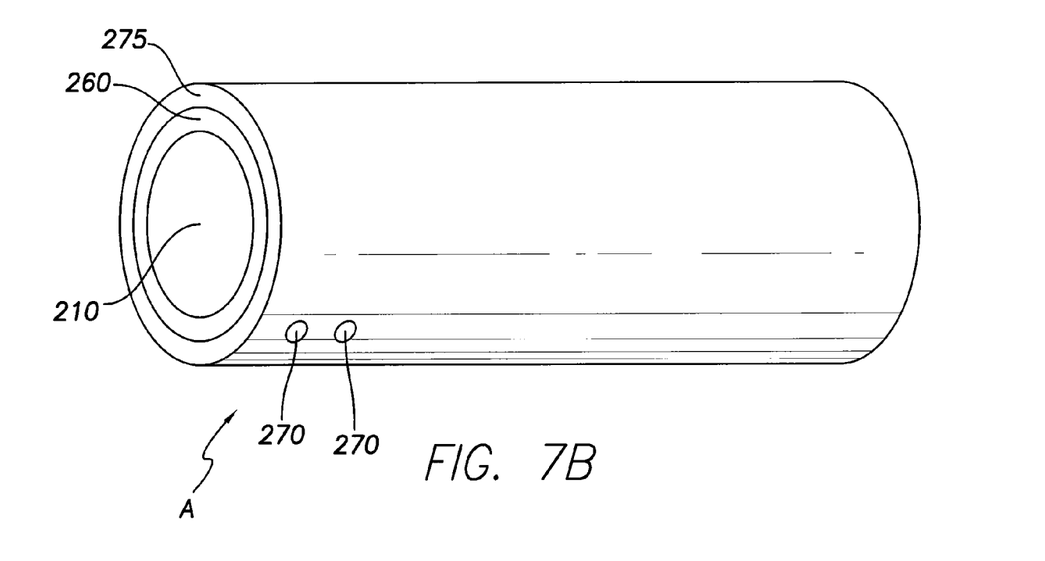
Figure 8A:
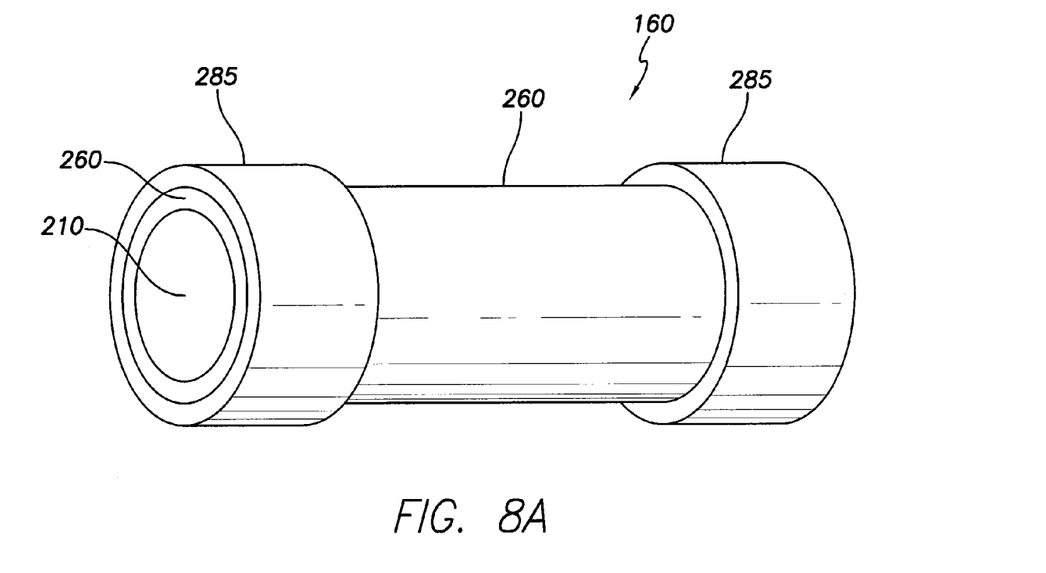
FIGS. 8A and 8B illustrate electrical contacts positioned over the ceramic layers of FIGS. 7A and 7B.
Figure 8B:
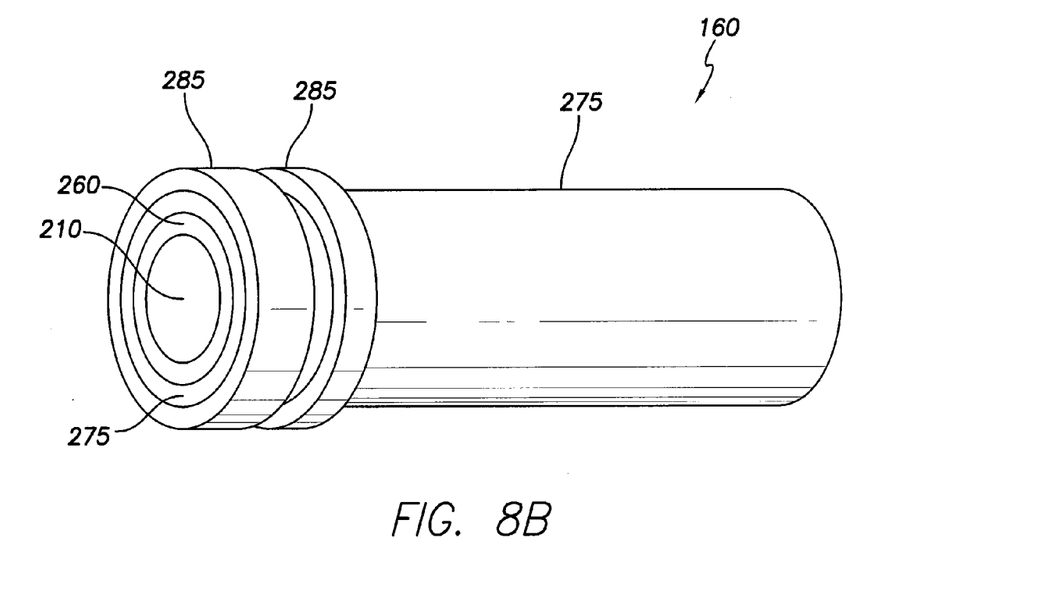

In different embodiments, the number of metallization layers (and overlaid ceramic layers) can be either even or odd of 1, 2, 3, 4, 5, 6, 7, 8, 9, 10, etc. and the self resonant inductor may be used as a tip self resonant inductor in the medical lead 10. For example, in some embodiments, an odd number of metallization layers will be used to result in terminal vias at opposite ends of the self resonant inductor as shown in FIGS. 7A and 9. If an even number of layers are implemented, such as two layers (e.g., ceramic layers 260 and 275), as shown in FIG. 7B, the vias 270 will be located on the same side of the self resonant inductor. Thus, if the self resonant inductor 160 only had two ceramic layers 260, 275 such that the outmost ceramic layer 277 of FIG. 9 was not present, then the vias 270 would be at one end of the self resonant inductor as indicated by arrow A in FIG. 7B. As a result, the self resonant inductor 160 would have electrical contacts 285 extending about ceramic layer 275 near a single end of the self resonant inductor 160, as shown in FIG. 8B. However, regardless of whether odd or even numbers of layers are employed, in some embodiments, a trace or other electrically conductive layer can be provided to extend from one end to the other such that an even number layered arrangement has terminals or contacts at opposite ends and an odd number layered arrangement has terminals or contacts at the same end. In fact, such traces may be employed to relocate the terminals or contacts anywhere along or on the self resonant inductor 160 (including the butt ends of the self resonant inductor) where convenient for manufacturing.

Figure 10:
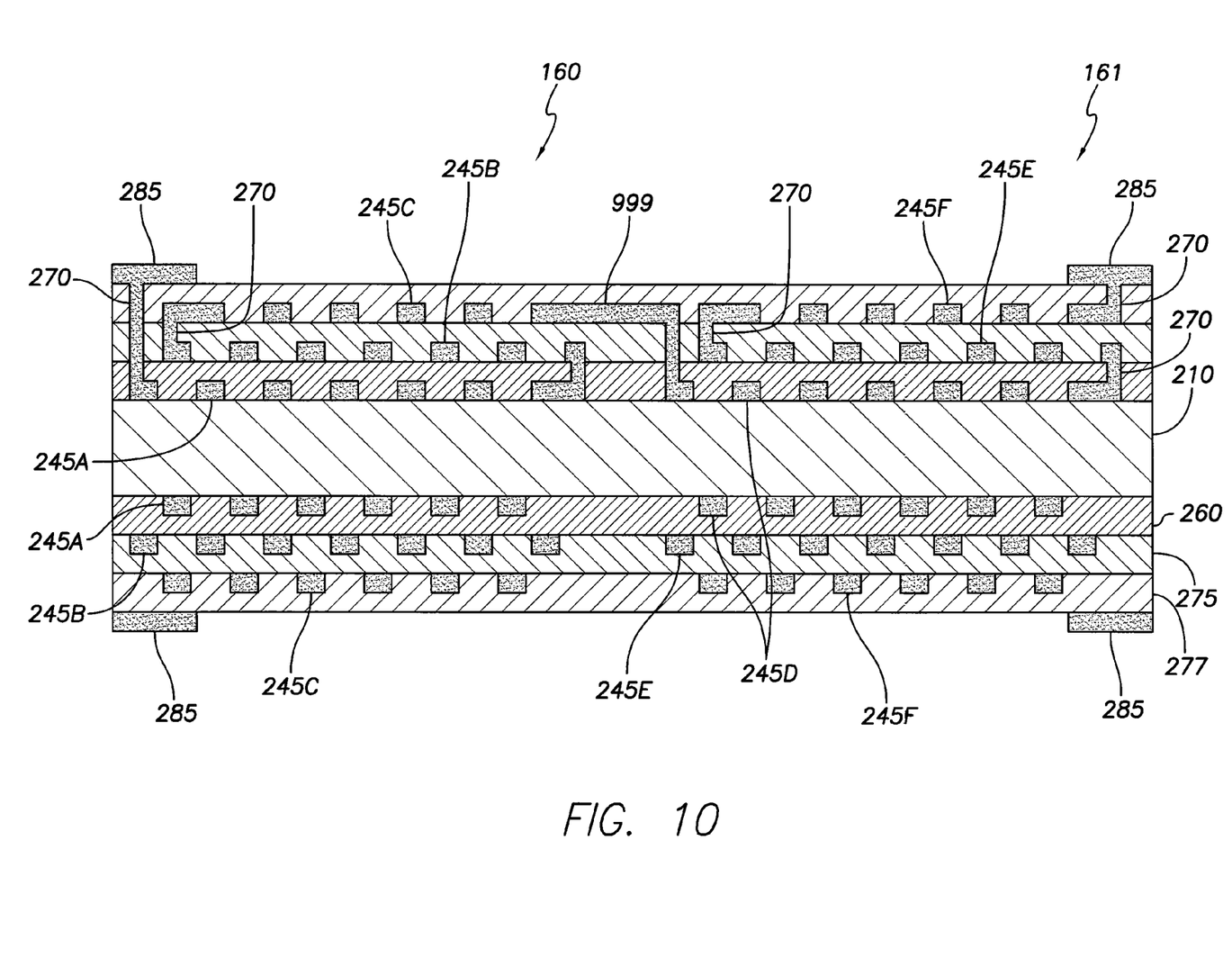
FIG. 10 is a longitudinal cross section of multiple self resonant inductors formed on and sharing the same ceramic layers.

As mentioned above and indicated in FIG. 10, multiple self resonant inductors 160, 161 may be formed on and share the same ceramic layers 260, 275, 277. The first set of helical metallization layers 245A-C may form the first self resonant inductor 160, the second set of helical metallization layers 245D-F may form the second self resonant inductor 161, and both sets of helical metallization layers 245A-C and 245D-F are formed on and share the same ceramic layers 260, 275, 277. Each self resonant inductor 160, 161 may be configured for a different frequency. For example, the first self resonant inductor 160 may be configured for 64 MHz and the second self resonant inductor 161 may be configured for 128 MHz. The two self-resonant inductors are connected in series as shown in FIG. 10 by inner-conductor 999. In yet other embodiments, more than two self resonant inductors may be present on the same ceramic layers to address more than two frequencies.

Once all of the layers have been created, a final metallization layer is deposited over the last ceramic layer, as indicated at block 280 (FIG. 3). The final metallization layer may be deposited using a vapor deposit technique or other suitable process. The final metallization layer may be any high conductivity biocompatible metallic or metallic alloy. As can be understood from FIGS. 8A and 9 and block 290 of FIG. 3, the final metallization layer may be etched or laser ablated to form terminals or electrical contacts 285 for connection to lead wires 185, 190 leading to other components of the lead 10, as illustrated in FIG. 2. As indicated in FIGS. 7A, 8A and 9, where the self resonant inductor 160 has an odd number of helical metallization layers, the vias 270 and electrical contacts 285 may be located at opposite ends of the self resonant inductor 160. As shown in FIGS. 7B and 8B, if an even number of helical metallization layers were created, then the vias 270 and electrical contacts 285 may be formed on the same side of the self resonant inductor 160. It should be understood, however, that although the electrical contacts 285 have been illustrated as rings that completely encircle the ceramic layers 260 and 275, the electrical contacts 285 may take on any suitable form or shape to provide compatibility with existing lead connections and/or to fit a particular design. In one embodiment, an self resonant inductor 160 may be configured such that a most distal electrical contact 285 of the self resonant inductor 160 may be used as lead electrode if the self resonant inductor 160 is located within the lead body such that the most distal electrical contact 285 forms a portion of the lead body surface and is formed of a biocompatible material.

The foregoing describes some example embodiments to achieve the high Q self resonant inductor using a high dielectric constant ceramic insulation between windings of the self resonant inductor to increase the interwinding capacitance and, thus, reduce the number of turns required for the self resonant inductor. The reduced number of turns reduces the series resistance of the self resonant inductor, thereby resulting in reduced $I^2R$ heating during MRI RF application.

Although the present invention has been described with reference to illustrated embodiments, persons skilled in the art will recognize that changes may be made in form and detail without departing from the spirit and scope of the invention. Indeed, in other embodiments, a metallic wire or metallic alloy wire, in place of the deposited metallic layers discussed above, may be used to form the hexical pattern, thus forming a coil inductor. Additionally or alternatively, other materials rather than ceramics may be used to provide the high dielectric constant between windings. Accordingly, the specific embodiments described herein should be understood as examples and not limiting the scope of the disclosure.

What is claimed is:

1. An implantable medical lead comprising:
a resonant filter comprising an inductor having a parasitic capacitance, the inductor and parasitic capacitance forming a parallel resonant LC filter, the inductor having a first layer comprising: a first helical metallic member located on an elongated member, the first helical metallic member comprising a first terminal end located near a proximal end of the elongated member and a second terminal end located near a distal end of the elongated member; and a dielectric ceramic material coaxially covering the elongated member and the first helical metallic member, wherein the dielectric material between turns of the helical metallic member forms the parasitic capacitance and wherein the dielectric ceramic material encapsulates the first helical metallic member and includes first and second apertures located over the first and second terminal ends, respectively, of the first metallic helical member such that the terminal ends are accessible through the apertures; and
a lead body including a lead connector end on a proximal end of the lead body and an electrode on a distal end of the lead body, the lead connector end including an electrical contact, the self resonant inductor supported on the lead body, the first terminal being in electrical communication with the electrical contact of the lead connector end via a first electrical pathway extending through the first aperture, the second terminal being in electrical communication with the electrode via a second electrical pathway extending through the second aperture.

2. The implantable medical lead of claim 1, wherein the inductor further comprises a second layer comprising: a second helical metallic member located on the dielectric ceramic material of the first layer, the second helical metallic member comprising a third terminal end located near a proximal end of the elongated member and a fourth terminal end located near a distal end of the elongated member, the fourth terminal end conductively coupled to the second terminal end of the first layer, the third terminal end forming part of the second electrical pathway.

3. The implantable medical lead of claim 2, wherein the inductor further comprises a second dielectric ceramic material coaxially covering the dielectric ceramic material of the first layer and the second helical metallic member, the second dielectric ceramic material encapsulating the second metallic helical member.

4. The implantable medical lead of claim 3, wherein the inductor further comprises a first electrical contact on the second ceramic material and located near the distal end of the elongated member, the first electrical contact being conductively coupled to the fourth terminal end.

5. The implantable medical lead of claim 4, wherein the first electrical contact forms at least part of the electrode.

6. The implantable medical lead of claim 1, wherein the first helical metallic member comprises a metal or metallic alloy vapor deposited on the surface of the elongated member and chemically etched or laser ablated to create the helical pattern.

7. The implantable medical lead of claim 1, wherein the helical metallic member comprises a metal or metallic alloy wire wound about the elongated member.

8. The implantable medical lead of claim 1, wherein the elongated member comprises a ceramic rod or ceramic tube and wherein the dielectric ceramic material comprises a high-K dielectric ceramic material.

9. The implantable medical lead of claim 8, wherein the high-K dielectric ceramic material comprises barium titanite.

10. An implantable medical lead comprising:
a body including a distal portion with an electrode and a proximal portion with a lead connector end; and
an electrical pathway extending between the electrode and lead connector end, the electrical pathway including an inductor having a parasitic capacitance, the inductor and parasitic capacitance forming a parallel resonant LC filter, wherein the self resonant inductor comprises one or more layers comprising a helical metallic pattern on a dielectric ceramic material and a ceramic layer coaxially covering the helical metallic pattern wherein the dielectric material between turns of the helical metallic member forms the parasitic capacitance.

11. The implantable medical lead of claim 10, wherein the helical metallic pattern comprises a vapor deposited metal or metallic alloy that has been chemically etched or laser ablated to form the helical pattern.

12. The implantable medical lead of claim 10, wherein the inductor comprises an odd number of layers of a helical metallic pattern on a dielectric ceramic material.

13. The implantable medical lead of claim 10, wherein the self resonant inductor has a self resonant frequency of approximately 64 MHz or approximately 128 MHz.

14. The implantable medical lead of claim 10, further comprising one or more additional self resonant inductors comprising one or more layers comprising a helical metallic pattern on the dielectric ceramic material and the ceramic layer coaxially covering the helical metallic pattern.

* * * * *